United States Patent [19]

Columbus et al.

[11] Patent Number: 5,050,617
[45] Date of Patent: Sep. 24, 1991

[54] REMOVABLE HANDLE AND MEANS FOR ATTACHMENT TO A SYRINGE OR PHLEBOTOMY DEVICE

[75] Inventors: Richard L. Columbus, Rochester; Johannes J. Porte, Webster, both of N.Y.

[73] Assignee: Eastman Kodak Company, Rochester, N.Y.

[21] Appl. No.: 481,839

[22] Filed: Feb. 20, 1990

[51] Int. Cl.⁵ ............................................. A61B 5/00
[52] U.S. Cl. .................................. 128/763; 604/228
[58] Field of Search ............... 604/228, 110; 128/760, 128/763, 764, 765

[56] References Cited

U.S. PATENT DOCUMENTS

| | | | |
|---|---|---|---|
| 3,045,674 | 7/1962 | Goldberg | 128/218 |
| 4,014,322 | 3/1977 | Shah | 128/760 |
| 4,507,117 | 3/1985 | Vining et al. | 604/196 |
| 4,677,980 | 7/1987 | Reilly et al. | 128/655 |
| 4,892,107 | 1/1990 | Haber | 604/110 |

FOREIGN PATENT DOCUMENTS 218668 12/1961 Fed. Rep. of Germany .

Primary Examiner—Kyle L. Howell
Assistant Examiner—Robert L. Nasser, Jr.
Attorney, Agent, or Firm—Dana M. Schmidt

[57] ABSTRACT

A combination is disclosed of a handle and a member that is either a phlebotomy device or a drug-injecting syringe. The handle removably attaches by a mating pivot pin and aperture disposed relative to the axis of the handle and the member to ensure that the unlatched configuration is geometrically different from the latched configuration. Latching is achieved by a hook member on one that engages a recessed groove on the other, simply by pivoting the handle until its axis coincides with the axis of the member.

4 Claims, 2 Drawing Sheets

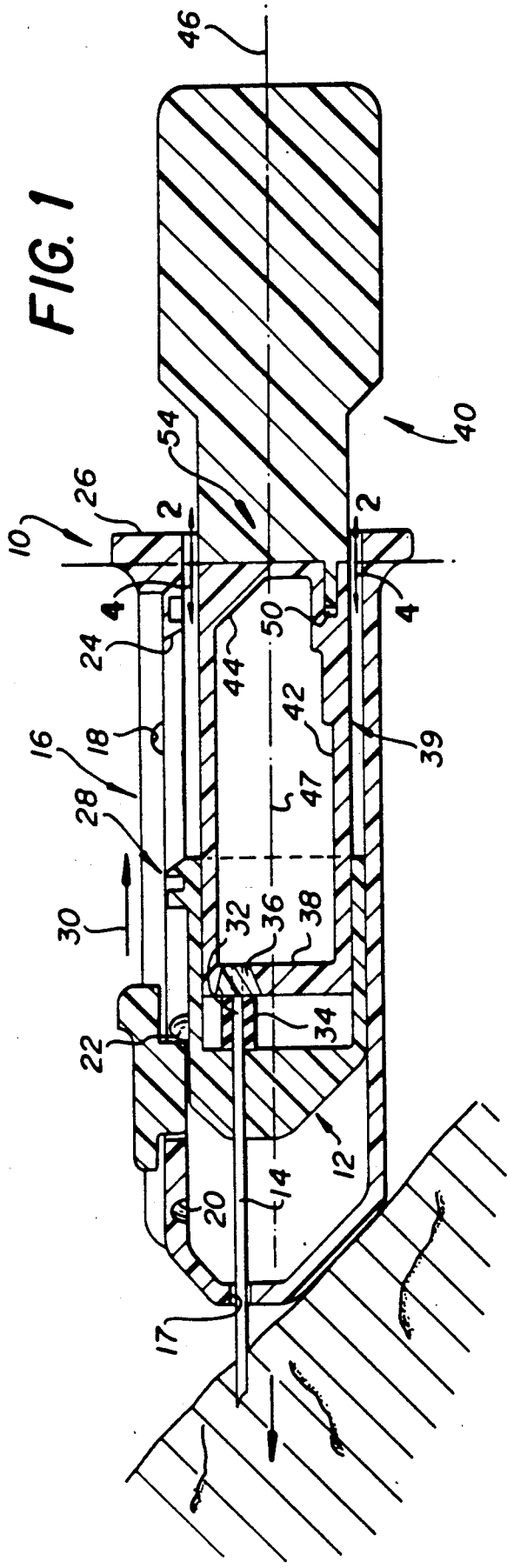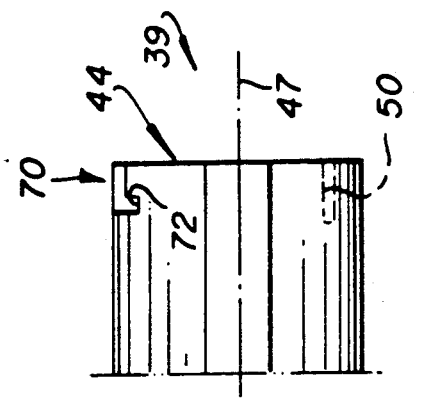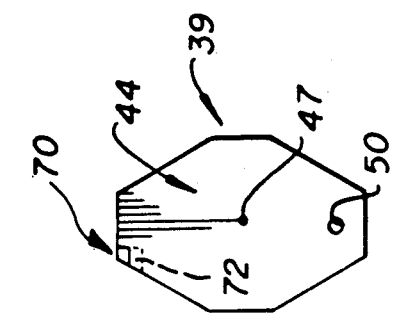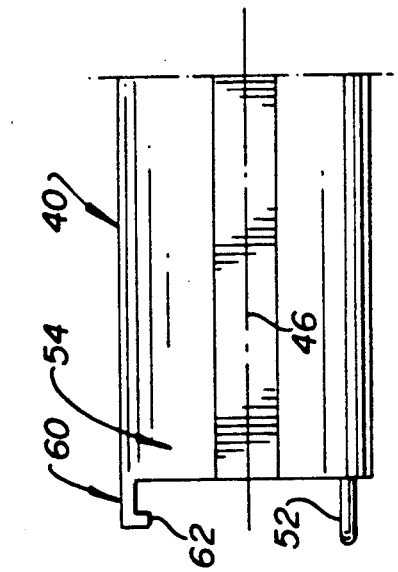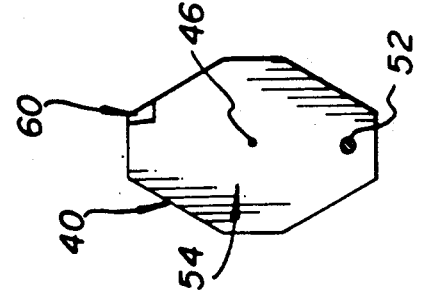

REMOVABLE HANDLE AND MEANS FOR ATTACHMENT TO A SYRINGE OR PHLEBOTOMY DEVICE

FIELD OF THE INVENTION

The invention relates to handle for phlebotomy devices or drug-injecting syringes, particularly those handles that are removable.

BACKGROUND OF THE INVENTION

Blood collecting devices, known as phlebotomy tubes, are usually evacuated tubes that are inserted into syringes to collect blood from a vein. Typically, several such tubes are sequentially inserted into a syringe while that syringe remains injected into a patient. Thus, the tubes usually have gripping means built into the tube to allow their manipulation in the manner stated. That is, the outside of the tube is the gripping surface. However, further processing of the tubes is needed after blood collection, and any extensive gripping portion can be objectionable if it gets in the way of such processing. Particularly this becomes true if the collecting container is reduced in size, as then a handle must be added that serves no other function.

Thus, it would be convenient if a phlebotomy tube could be provided with a removable handle that is used only when the tube is put into or taken out of the syringe.

Removable handles have been typical of drug-injecting syringes. Generally such handles involve a friction fit with the piston used to push the drug out of a prepackaged container. Examples of such a construction are shown in, e.g., U.S. Pat. Nos. 3,045,674 and 4,507,117, as well as German Patentschrift No. 218,668. Such friction fit, however, is not a very secure engagement, so that there is no surety that accidental disengaging will not occur.

To improve upon such problems of friction fits, a rotating latch mechanism is described for a drug injection syringe in U.S. Pat. No. 4,677,980, that rotates 90° between an engaged connection, FIG. 9, and a disengageable connection, FIG. 10. However, this construction renders it difficult to ascertain whether the handle is locked or not, as both conditions present the same overall appearance of the handle vis-a-vis the rest of the device. That is, the handle is rotated about a common axis with the syringe so that its apparent geometry vis-a-vis the syringe does not markedly change so as to suggest it is unlocked.

As far as can be ascertained, removable handles have never been proposed for phlebotomy devices, prior to this invention. Such a fact tends to discourage any reduction in size of the phlebotomy device, since the built-in gripping surface alone mitigates against size reduction.

Thus, prior to this invention, there has been a need for a removable handle for either a phlebotomy tube or a piston of a drug-injecting syringe that avoids the above-noted problems.

SUMMARY OF THE INVENTION

I have solved the above-noted need by a handle construction that differs markedly in its position when it is unlocked, compared to its locked relationship with the syringe or phlebotomy device.

More specifically, there is provided in accord with one aspect of the invention a phlebotomy device comprising a blood collection container having at least one liquid-confining compartment, two opposite ends and a longitudinal axis extending between the ends, one of the ends being a liquid access end constructed to mate with a needle to draw blood into the compartment, and a removable handle on the other end, the handle and the other end including attaching means for removably attaching the handle to the other end.

In accord with another aspect of the invention, there is provided a removable handle in combination with a member selected from a blood collecting device and a drug-injecting syringe, the device or syringe being provided with a needle for transmission of blood or a drug into or out of the device or syringe, respectively, the handle and the device or syringe having when assembled a central longitudinal axis, and further including a pivot pin in either the handle, or the device or syringe, and an aperture in the device or syringe, or handle, respectively, shaped and positioned to frictionally mate with the pin, the pin and the aperture being offset from and extending parallel to the axis, and further including latching means for latching the handle and the device or syringe together to prevent the pin and the aperture from being axially separated by opposing forces applied along the axis.

Thus, it is an advantageous feature of the invention that a phlebotomy device or syringe can be provided with a removable handle that has a positive engagement that is geometrically indicative of its latched or unlatched condition.

It is a related advantageous feature of the invention that such a combination of handle and phlebotomy device or syringe can feature a reduction in size, except for the handle, that permits subsequent processing to proceed without the handle, using smaller apparatus.

Other advantageous features will become apparent upon reference to the following Description of the Preferred Embodiments, when read in light of the attached drawings.

BRIEF DESCRIPTION OF THE DRAWINGS

FIG. 1 is an elevational view in section of a phlebotomy device constructed with a handle of this invention;

FIG. 2 is a section view of the handle taken generally along the line 2—2 of FIG. 1;

FIG. 3 is a fragmentary side elevational view of the handle shown in FIG. 2;

FIG. 4 is an end elevational view of the phlebotomy container taken generally along the line 4—4 of FIG. 1;

FIG. 5 is a fragmentary side elevational view of the container shown in FIG. 4;

DESCRIPTION OF THE PREFERRED EMBODIMENTS

Figure 6:
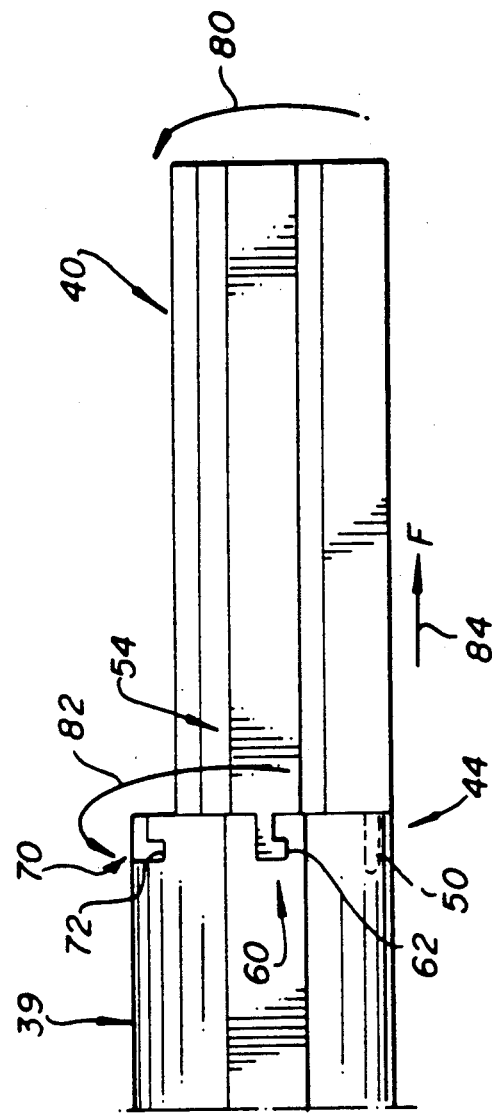
FIG. 6 is a fragmentary side elevational view showing the movement of the handle to latch it in place.

The invention is described particularly in reference to the preferred embodiments featuring certain phlebotomy devices and syringes for, respectively, blood collection and drug injection. In addition, it is useful regardless of the design of the phlebotomy device or syringe, and regardless of whether the syringe is used with drugs or some other material.

Turning first to FIG. 1, any phlebotomy device 10 can be provided with a handle 40 of the invention. Preferably, device 10 comprises a needle mounting member 12 in which a needle 14 is permanently embedded, member 12 in turn being slidable mounted in a safety shield or housing 16. Such a shield cooperates with member 12 as described in commonly-owned U.S. Application Ser. No. 481,838 cofiled herewith and entitled "Needle Device for Safely Collecting Blood or Injecting Drugs". However, such a shield is optional and can be omitted. If included, shield 16 has a needle aperture 17 and recesses 18 and 20 that coact with one or more detents 22 on member 12 to releasably hold the needle and mounting member 12 in one of two positions. In addition, locking tab 24 is formed at end 26 of shield 16, to cooperate with a latch 28 on member 12 to permanently hold the needle withdrawn after all blood is collected and the mounting member is withdrawn (arrow 30).

With or without the shield 16, needle 14 includes an end 32 that projects into member 12, with a collapsible sleeve 34 covering it. This end is designed to penetrate a septum 36 at one end 38 of a blood-collecting container 39, as is conventional. The container includes at least one liquid-confining compartment 42, and a longitudinal axis 47.

In accordance with the invention, opposite end 44 of container 39 has removably attached thereto, handle 40. Handle 40 has an axis 46, FIG. 3, that insures that when the handle is latched, FIG. 1, axis 46 coincides with axis 47 of container 39.

To provide for a positive latching of the handle, in a manner that geometrically distinguishes the latched condition from the unlatched condition, the following features are included:

End 44 of container 39 has an aperture 50 that extends parallel to axis 47, FIG. 4. A corresponding, mating pivot pin 52 projects from end 54 of handle 40, FIGS. 2 and 3, also parallel to axis 46, in position to line up with aperture 50 when disposed so that the axis 46 of handle 40 is aligned with axis 47. However, to insure that the unlatched configuration of handle 40 is distinguishable from the latched one, pin 52 and aperture 50 are disposed to be offset from axis 46 and 47, respectively.

The positive latching of the handle to container 39 is further achieved by a hook or bayonet member 60 mounted on, e.g., handle 40, FIG. 3, that slides into a mating groove 70 in end 44 of container 39, FIG. 4. Member 60 has a hook end 62 that projects into the handle toward axis 46, and cooperates with a recess 72 that also projects inwardly of container 39, FIG. 5, towards axis 47.

The assembly of handle 40 into its latched position is shown in FIG. 6. End 54 is abutted against end 44 of container 39 so that pin 52 is inserted into aperture 50, and the handle is rotated, arrow 80, to bring hook member 60 into groove 70 on container 39. When hook end 62 seats into recess 72, arrow 82, the latching is complete and any axially directed force F, arrow 84, is ineffective in separating handle 40 from container 39.

After blood collection is complete, handle 40 and device 39 are pulled out of housing 16, and the handle is removed. Thereafter, device 39 can be further processed to achieve serum separation, by conventional techniques.

Handle 40 has several advantages stemming from its construction. When it is fully latched to container 39, the latching is a positive engagement that cannot slip, as some frictional engagements are capable of doing. Furthermore, the latched and unlatched configurations are, by reason of their different axial alignments, clearly distinguishable one from the other (compare FIGS. 1 and 6), so that the user is able to identify which condition is present simply from the geometry. Still further, the use of the removable handle permits device 39, FIG. 1, to be greatly reduced in size to the point at which it fits totally inside housing 16, FIG. 1, thus becoming non-manipulable without the handle. For example, the total length of device 39 can be reduced to only 2.5 cm (one inch). This is particularly useful as blood draws are reduced in volume to supply analyzers that need much less sample.

It will be readily appreciated that pin 52 and aperture 50 can be reversed (not shown) so that the pin is on container 39. Likewise, member 60 and groove 70 can be reversed, so that member 60 is on container 39.

Figure 7:
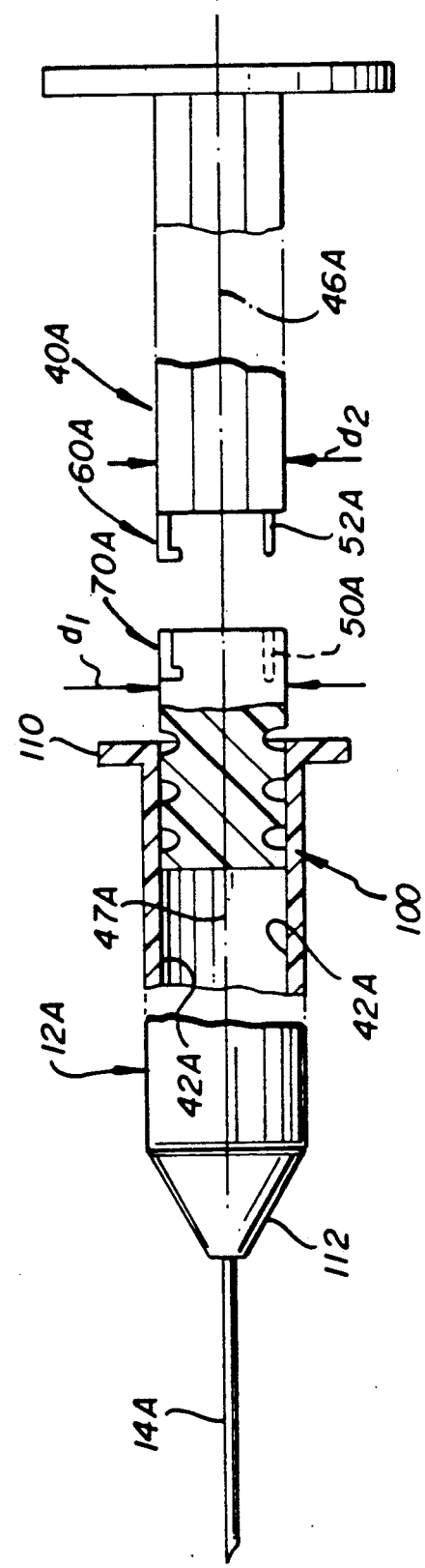
FIG. 7 is a fragmentary elevational view of the use of the handle of the invention with a piston in a drug-injecting syringe.

It will also be appreciated that the removable handle will readily attach to a piston of a drug-injecting syringe, FIG. 7. Parts similar to those previously described bear the same reference numeral, to which the distinguishing suffix A has been appended.

Thus, handle 40A is readily attachable and removable from a piston 100 having an O.D. "$d_1$", where the O.D. "$d_2$" of handle 40A preferably is slightly less than $d_1$. Piston 100 slides into end 110 within compartment 42A of drug-delivery syringe 12A which mounts a needle 14A at opposite end 112. The syringe construction is conventional, so that no further discussion is required.

The engagement of handle and piston is substantially the same as for the previous embodiment—pivot pin 52A is inserted into aperture 50A, and the handle rotated until member 60A latches into groove 70A in the surface of piston 100 and axis 46A of handle 40A coincides with axis 47A of piston 100. Thereafter, piston 100 can be pushed into container 39A to push the liquid contents out of needle 14A. The advantages of handle 40 enumerated above for the phlebotomy device accrue as well for handle 40A.

The invention has been described in detail with particular reference to certain preferred embodiments thereof, but it will be understood that variations and modifications can be effected within the spirit and scope of the invention.

What is claimed is:

1. A phlebotomy device comprising a blood collection container having at least one liquid-confining compartment, two opposite ends and a longitudinal axis extending between said ends, one of said ends being a liquid access end constructed to mate with a needle to draw blood into said compartment, and a removable handle on said other end, said handle and said other end including attaching means for removably attaching said handle to said other end by rotation of said handle, said attaching means comprising, as part of said handle or said other end, a mating pin and aperture extending parallel to and displaced from said axis, and latching means for preventing said pin from sliding out of said aperture when said latching means are engaged so that said handle pivots away from said axis when it is unlocked.

2. A removable handle in combination with a member selected from a blood collecting device and a drug-injecting syringe, said device or syringe being provided with a needle for transmission of blood or a drug into or out of the device or syringe, respectively, said handle and said device or syringe having when assembled a central longitudinal axis, and further including a pivot pin in either said handle, or said device or syringe, and an aperture in said device or syringe, or handle, respectively, shaped and positioned to frictionally mate with said pin, said pin and said aperture being offset from and extending parallel to said axis, and further including latching means for latching said handle and said device or syringe together to prevent said pin and said aperture from being axially separated by opposing forces applied along said axis.

3. A removable handle in combination with a member comprising a phlebotomy tube, said handle and tube having when assembled a central longitudinal axis, and further including a pivot pin in one of said tube and said handle, and an aperture in the other of said tube and said handle to frictionally mate with said pin, said pin and said aperture being offset from and extending parallel to said axis, and further including latching means for latching said handle and said member together to prevent said pin and said aperture from being axially separated by opposing forces applied along said axis.

4. A combination as defined in claim 2 or 3, wherein said latching means comprise a hook on one of said member and said handle and latch groove on the other of said member and said handle to receive said latch in a temporary locked configuration, said latch and groove when engaged preventing translation separation of said handle from said member.

* * * * *